United States Patent
Griffiths

(10) Patent No.: US 6,953,567 B2
(45) Date of Patent: Oct. 11, 2005

(54) FLUORINATION OF PROTEINS AND PEPTIDES FOR F-18 POSITRON EMISSION TOMOGRAPHY

(75) Inventor: Gary L. Griffiths, Morristown, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 359 days.

(21) Appl. No.: 10/071,247

(22) Filed: Feb. 11, 2002

(65) Prior Publication Data

US 2002/0119096 A1 Aug. 29, 2002

Related U.S. Application Data

(62) Division of application No. 09/644,706, filed on Aug. 24, 2000, now Pat. No. 6,358,489, which is a division of application No. 09/146,318, filed on Sep. 3, 1998, now Pat. No. 6,187,284.
(60) Provisional application No. 60/057,485, filed on Sep. 3, 1997.

(51) Int. Cl.[7] .................. A61K 101/02; A61K 49/14; A61K 49/16; G01N 33/534; C07K 16/00
(52) U.S. Cl. .................. 424/1.19; 424/9.4; 424/52; 424/193.1; 435/7.1; 530/391.3; 530/328
(58) Field of Search ................ 424/1.49, 1.53, 424/1.57, 9.1; 530/387.3, 396.3, 391.3, 328

(56) References Cited

PUBLICATIONS

Kuby et al, 1994, Immunology, Second edition, pp. 86–96.*
Colman et al, 1994, A structural view of immune recognition by antibodies, pp. 33–36.*

* cited by examiner

*Primary Examiner*—Christina Chan
*Assistant Examiner*—Phuong Huynh
(74) *Attorney, Agent, or Firm*—Heller Ehrman LLP

(57) ABSTRACT

Thiol-containing peptides can be radiolabeled with fluorine-18 (F-18) by reacting a peptide comprising a free thiol group with an F-18-bound labelling reagent which also has a group that is reactive with thiols. The resulting F-18-labeled peptides may be targeted to a tissue of interest using bispecific antibodies or bispecific antibody fragments having one arm specific for the F-18-labeled peptide or a low molecular weight hapten conjugated to the F-18-labeled peptide, and another arm specific to the targeted tissue. The targeted tissue is subsequently visualized by clinical positron emission tomography.

12 Claims, No Drawings

FLUORINATION OF PROTEINS AND PEPTIDES FOR F-18 POSITRON EMISSION TOMOGRAPHY

RELATED APPLICATIONS

This application is a divisional of application Ser. No. 09/644,706, filed Aug. 24, 2000, now U.S. Pat. No. 6,358,489 which is a divisional of application Ser. No. 09/146,318, filed Sep. 3, 1998, now U.S. Pat. No. 6,187,284 which claims the benefit of U.S. Provisional Application No. 60/057,485, filed Sep. 3, 1997, all of which are hereby incorporated by reference.

BACKGROUND OF THE INVENTION

1. Field of the Invention

The present invention concerns methods for radiolabeling proteins and peptides with fluorine-18 (F-18). More particularly, these proteins and peptides are radiolabeled with F-18 by reacting a thiol group contained therein with an F-18-bound labeling reagent which also has a group that is reactive with thiols. The resulting F-18-labeled proteins and peptides are useful in imaging targeted tissue by clinical positron emission tomography.

2. Description of the Related Art

Positron emission tomography (PET) is a high resolution, non-invasive, imaging technique for the visualization of human disease. In PET, 511 keV gamma photons produced during positron annihilation decay are detected. In the clinical setting, fluorine-18 (F-18) is one of the most widely used positron-emitting nuclides. F-18 has a half-life (t½) of 110 minutes, and emits β+particles at an energy of 635 keV. It is 97% abundant.

The short half-life of F-18 has limited or precluded its use with longer-lived specific targeting vectors such as antibodies, antibody fragments, recombinant antibody constructs and longer-lived receptor-targeted peptides. In addition, complicated chemistry has been required to link the inorganic fluoride species to such organic targeting vectors. In typical synthesis methods, an intermediate is radiofluorinated, and the F-18-labeled intermediate is purified for coupling to protein amino groups. See, e.g., Lang et al., *Appl. Radiat. Isol.*, 45 (12): 1155–63 (1994); Vaidyanathan et al., *Bioconj. Chem.*, 5: 352–56 (1994).

These methods are tedious to perform and require the efforts of specialized professional chemists. They are not amenable to kit formulations for use in a clinical setting. Multiple purifications of intermediates are commonly required, and the final step, involving linkage to protein lysine residues, usually results in 30–60% yields, necessitating a further purification step prior to patient administration. In addition, these methods result in fluorinated targeting species which accumulate in the kidney, somewhat like radiometals.

It was recently reported that $^{18}$F-fluoroiodomethane ($^{18}$FCH$_2$I) is a useful intermediate for the fluorination of organic intermediates. Zheng et al., *J. Nuc. Med.*, 38: 177P (Abs. 761) (1997). In this process, diiodomethane is fluorinated with the F-18 ion by a room temperature reaction in acetonitrile solvent, resulting in up to a 40% yield. The $^{18}$FCH$_2$I is then distilled into reaction vials containing various strong nucleophiles in anhydrous acetonitrile and allowed to react at 80° C. for fifteen minutes. Nucleophilic attack by carboxylates, thiolates, phenolates, and amines in particular, replaces the remaining iodine of $^{18}$FCH$_2$I, with overall yields of 10 to 35%. The reaction products can be purified by reverse-phase HPLC. Fluoromethyl diethylamine, fluoromethyl benzoate, fluoromethyl benzyl thioether and fluoromethyl 4-(2-hydroxy-3-aminopropoxy)-carbazole have been made by this method.

As discussed above, the currently available methods for labelling protein-based targeting vectors with F-18 are unsuitable. There is a need, therefore, for a simple, efficient method for incorporating the F-18 radionuclide into peptide-containing targeting vectors, such as proteins, antibodies, antibody fragments, and receptor-targeted peptides, to allow the use of such targeting vectors in routine clinical positron emission tomography.

SUMMARY OF THE INVENTION

The present invention provides methods for incorporating the F-18 radionuclide into peptide-containing targeting vectors.

In accordance with one embodiment of the invention there is provided a method for radiolabeling thiol-containing peptides with fluorine-18 (F-18), comprising reacting a peptide comprising a free thiol group with a labelling reagent having the general formula $^{18}$F—(CH$_2$)$_m$—CR$_1$R$_2$—(CH$_2$)$_n$—X, wherein:

n is 0, 1 or 2;

m is 0, 1 or 2;

and n+m is 0, 1, or 2;

X is selected from the group consisting of iodide, bromide, chloride, azide, tosylate, mesylate, nosylate, triflate, unsubstituted maleimide, maleimide substituted with one or two alkyl groups, and maleimide substituted with a sulfonate group; and R$_1$ and R$_2$ are the same or different and are selected from the group consisting of iodide, bromide, chloride, azide, tosylate, mesylate, nosylate, triflate, hydrogen, —CONH$_2$, carboxyl, hydroxyl, sulfonic acid, tertiary amine, quaternary ammoniumun, unsubstituted alkyl, substituted alkyl, —COOR', —CONR'$_2$ or COR', wherein the substituents of the substituted alkyl groups are selected from the group consisting of —CONH$_2$, carboxyl, hydroxyl, sulfonic acid, tertiary amine and quaternary ammonium and wherein R' is a C$_1$–C$_6$ alkyl or phenyl.

In accordance with another embodiment, there is provided a method for radiolabeling thiol-containing peptides with F-18, comprising reacting a peptide comprising a free thiol group with a F-18 fluorinated alkene, wherein at least one of the two double-bonded carbon atoms bears at least one leaving group selected from the group consisting of iodide, bromide, chloride, azide, tosylate, mesylate, nosylate and triflate.

In accordance with another embodiment of the invention, a peptide that has been radiolabeled with F-18 as described above is delivered to a targeted tissue using a bispecific antibody (bsMAb) or a bispecific antibody fragment (bsFab) containing at least one arm that is specific to the targeted tissue and at least one other arm that is specific to the F-18-labeled peptide or a low molecular weight hapten conjugated to the F-18-labeled peptide.

In this methodology, the bsMAb or the bsFab is administered to a patient and allowed to localize to the targeted tissue. Some time later (after the unbound bsMAb or the unbound bsFab is allowed to clear), the F-18-labeled peptide or the hapten conjugate thereof is administered to the patient. Since at least one of the arms of the bsMAb or the bsFab is specific to the F-18-labeled peptide or the hapten conjugated to the F-18-labeled peptide, the F-18-labeled peptide is also localized to the target. After the unbound F-18-labeled peptide or the unbound hapten conjugate thereof is allowed to clear, the target is then visualized by routine clinical positron emission tomography.

The bsMAb or bsFab is ideally monoclonal and humanized. Preferably, the F-18-labeled peptide contains a thiol group. Examples of suitable peptides are X-Gly-D-Tyr-D-Trp-Gly-D-Lys(X)-Gly-D-Tyr-D-Trp-OH wherein X represents a free or protected amino acid group, Ac-Cys(Y)-D-Tyr-D-Trp-Gly-D-Cys(Y)-Gly-D-Tyr-D-Trp-OH wherein Y represents a free or protected thiol group, and Ac-Gly-D-iodo-Tyr-D-Trp-Gly-D-Lys-(Ac)-Gly-D-iodo-Tyr-D-Trp-OH. The hapten can be a metal chelate complex comprising, for example, manganese, iron, or gadolinium which are useful in magnetic resonance imaging (MRI).

The bsMAb, bsFab, and associated methodologies described above are disclosed in U.S. Provisional Application Ser. No. 60/090,142 (entitled "Production and use of novel peptide-based agents for use with bispecific antibodies" and filed Jun. 22, 1998), the entire contents of which are herein incorporated by reference.

These and other objects and aspects of the invention will become apparent to the skilled artisan in view, of the teachings contained herein.

DETAILED DESCRIPTION OF THE INVENTION

The present invention provides simple and efficient methods for incorporating the F-18 radionuclide into peptide-containing targeting vectors, such as proteins, antibodies, antibody fragments and receptor-targeted peptides. For convenience, the term "peptide" is used below and in the claims to refer to proteins, antibodies, antibody fragments and receptor-targeted peptides. The methods of the present invention makes such targeting vectors available for routine clinical positron emission tomography.

Of all nucleophiles present on peptides, only the free thiol group can be rapidly alkylated at neutral pH and moderate temperature. The present invention takes advantage of this unique property of free thiol groups, and provides methods for labelling thiol-containing peptides with F-18.

In accordance with one embodiment, the method of the present invention comprises the following reaction:

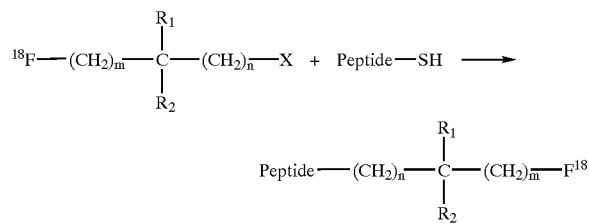

wherein n is 0, 1 or 2, m is 0, 1 or 2, and n+m is 0, 1, or 2, and X is a substitutable leaving group such as iodide, bromide, chloride, azide, tosylate, mesylate, nosylate, triflate and the like. Alternatively, X is maleimide or a substituted maleimide, substituted, for example with one or two alkyl groups or a sulfonate group. Examples of suitable substituted maleimides include 3-methylmaleimide, 3,4-dimethylmaleimide and 3-sulfo-maleimide. $R_1$ and $R_2$ can be the same or different and, as discussed in more detail below, are chosen for the desirable physical properties they bring to the reagent. In general, $R_1$ and $R_2$ can be selected from the same groups as X, and can be the same as or different from X. Alternatively, $R_1$ and $R_2$ each independently can be hydrogen, a substituted or unsubstituted linear or branched alkyl group, or a carbonyl function such as an ester, amide or ketone, for example, —COOR', —CONR'$_2$, or COR', where R' is a $C_1$–$C_6$ alkyl or phenyl. Examples of suitable $R_1$ and $R_2$ groups or substituents thereon also include groups which impart aqueous solubility, such as —CONH$_2$, carboxyl, hydroxyl, sulfonic acid and tertiary amine or quaternary ammonium.

In accordance with another embodiment of the invention, the peptide is labeled with an F-18 fluorinated alkene, wherein at least one of the two double-bonded carbon atoms bears at least one leaving group selected from the group consisting of iodide, bromide, chloride, azide, tosylate, mesylate, nosylate and triflate. Examples of suitable fluorinated alkenes include $^{18}$F—CH=CI$_2$, $^{18}$F—CI=CH$_2$, or $^{18}$F—CI=CI$_2$. The labeling reaction is analogous to the one described above.

The methods of present invention can be used to label any thiol-containing peptide. Of particular interest are peptides useful as targeting vectors. Examples of such targeting vectors include antibodies, F(ab')$_2$, F(ab)$_2$, Fab' and Fab fragments, single-chain sub-fragments such as sFvs, divalent constructs such as dsFvs, and polypeptides containing one or more free thiol groups. See Choi et al., *Cancer Res.*, 55: 5323–29 (1995). Further examples include antibody constructs such as antibodies comprising IgG$_3$ or IgG$_3$-F (ab')$_2$ frameworks. IgG$_3$'s have multiple hinge-region disulfide groups which can be reduced to generate multiple free thiol groups.

Peptides that originally do not comprise a free thiol group can be labelled in accordance with the present invention by first modifying the peptide to add a free thiol group by methods known to those skilled in the art. For example, the peptide can be thiolated with reagents such as 2-iminothiolane, or intrinsic disulfide bonds such as cystine residues can be reduced. A combination of both modifications also can be performed, such as the acylation of lysine residues with N-succinimidyl-3-(2-pyridylthio)-propionate (SPDP) followed by the controlled reduction of the appended disulfide bond.

In one embodiment of the present invention, the peptide is a Fab or Fab' fragment. These peptides have free thiol groups in their hinge-region, a site which is both specific and remote from the antigen-targeting sites.

To optimize the reaction with the thiol-containing peptides, the labelling reagent preferably has the following physical and chemical properties:

(1) The reagent is readily and rapidly synthesized from F-18.

(2) The reagent has adequate aqueous solubility in the neutral (4–8) pH range. By "adequate aqueous solubility" is meant that the reagent readily dissolves at up to a concentration comparable to a stoichiometric amount of the thiol-containing peptide used. If, for example, an antibody is being labeled, a typical antibody concentration is about 50 mg/mL, which corresponds to a molar concentration of about $3 \times 10^{-4}$ M. In this example, the reagent should be soluble at a concentration of about $3 \times 10^{-4}$ M. With lower molecular weight peptide species, more peptide will dissolve without precipitation, and more reagent can be used. Because F-18 is carrier-free, lower concentrations of fluorination agents also might be effective.

(3) The active halides of the reagent are not immediately hydrolyzed by water at neutral pH (pH 4–8). Thus, the halides should react more readily with SH or S$^-$ than with H$_2$O. As long as the reagent is not immediately hydrolyzed by water (or by neutral buffer solutions), the selectivity and reactivity of the thiol group ensures an efficient peptide labeling reaction.

(4) The leaving group X can be displaced rapidly, specifically, and near-quantitatively by free thiol moieties. A carbo-cationic center can be developed at the carbon atom which is attacked by the nucleophile, for example, $R_1$ and $R_2$ can be electron-withdrawing groups. The presence of electron-withdrawing groups alpha to the —C—X functional group also facilitates fast displacement of the X moiety. Examples of useful electron-withdrawing groups include —COR', —CONR', —CO$_2$R', —COOH, —CONH$_2$, and —SO$_3$H, where R' is a $C_1$–$C_6$ alkyl or phenyl.

In addition, the presence of more than one leaving group in the labelling reagent can be advantageous. Multiple leaving groups, such as iodo groups, attached to the same carbon atom produce steric strain. When a reaction comprises the departure of a single leaving group, this steric strain is relieved, imparting faster reaction kinetics to the thiol displacement of the X group. Thus, in accordance with one embodiment of the invention, the labeling reagent comprises at least two leaving groups, such as two iodo groups.

In accordance with one embodiment of the present invention, the peptide is labeled with a labelling reagent of the general formula $^{18}F$—$(CH_2)_m$—$CR_1R_2$—$(CH_2)_n$—X, wherein n is 0, 1 or 2, m is 0, 1 or 2, and n+m is 0, 1, or 2, and X is a substitutable leaving group such as iodide, bromide, chloride, azide, tosylate, mesylate, nosylate, triflate, and the like. Alternatively, X is maleimide or a substituted maleimide, substituted, for example with one or two alkyl groups. Examples of suitable substituted maleimides include 3-methylmaleimide, 3,4-dimethylmaleimide and 3-sulfo-maleimide. $R_1$ and $R_2$ can be the same or different and, as discussed above, are chosen for the desirable physical properties they bring to the reagent. In general, $R_1$ and $R_2$ can be selected from the same groups as X, and can be the same as or different from X. Alternatively, $R_1$ and $R_2$ each independently can be hydrogen, a substituted or unsubstituted linear or branched alkyl group, or a carbonyl function such as an ester, amide or ketone, for example, —COOR', —CONR'$_2$, or COR', where R' is a $C_1$–$C_6$ alkyl or phenyl. Examples of suitable $R_1$ and $R_2$ groups or substituents thereon also include those which impart aqueous solubility, such as —CONH$_2$, carboxyl, hydroxyl, sulfonic acid and tertiary amine or quaternary ammonium.

Examples of suitable labelling reagents include $^{18}F$—$CI_3$; $^{18}F$—$CHI_2$; $^{18}F$—$CI_2COOH$; $^{18}F$—$CI_2COOCH_3$; $^{18}F$—$CI_2CH_2OH$; $^{18}F$—$CHICH_2OH$; $^{18}F$—$CHIOOOCH_3$; $^{18}F$—$CI_2CH_2COOH$; $^{18}F$—$CI_2CH_2N^+(CH_3)_3$; $^{18}F$—$CI_2CH_2$maleimide; $^{18}F$—$CI_2$—$CONH_2$; $^{18}F$—$CI_2$—$CO_2CH_3$; $^{18}F$—$CHBr_2$; $^{18}F$—$CBr_2CH_2CH_2$—$SO_3H$; $^{18}F$—$CH_2CI_2COOH$; $^{18}F$—$CH_2CI_2CONH_2$; $^{18}F$—$CHICO_2CH_3$; $^{18}F$—$CI_2CONH_2$; $^{18}F$—$CHICONH_2$; $^{18}F$—$CBr_2CH_2OH$; $CF_3COCI_2$—$^{18}F$; $CH_3COCBr_2$—$^{18}F$; $^{18}F$—$CHBrCN$; $^{18}F$—$CI_2CHCN$; $CBrF_2$—$^{18}F$; $^{18}F$—$CBr (CONH_2)_2$, and $C_6H_5$—$COCBr_2$—$^{18}F$. Other suitable labeling reagents will be apparent to those skilled in the art.

The labeling reagent can be made by the F-18 fluorination of a corresponding compound. The following are examples of compounds which can be fluorinated to make the labeling reagents set forth above: $CI_4$; $CHI_3$; $CHI_2COOCH_3$; $CI_3COOH$; $CI_3COOCH_3$; $CI_3CH_2OH$; $CHI_2CH_2OH$; $CI_3CH_2COOH$; $CI_3CH_2N^+(CH_3)_3$; $CI_3CH_2$—maleimide; $CI_3$—$CONH_2$; $CI_3$—$CO_2CH_3$; $CHIBr_2$; $CIBr_2CH_2CH_2$—$SO_3H$; $CH_2CI_3COOH$; $CH_2CI_3CONH_2$; $CHI_2CO_2CH_3$; $CI_3CONH_2$; $CHI_2CONH_2$; $CBr_3CH_2OH$; $CF_3COCI_3$; $CH_3COCBr_3$; $Br_2CHCN$; $CI_3CHCN$; $CBr_2F_2$; $CBr_2(CONH_2)_2$ and $C_6H_5$—$COCBr_3$. Other suitable compounds will be apparent to those skilled in the art.

In accordance with another embodiment of the invention, the labeling reagent is an F-18 fluorinated alkene, wherein at least one of the two double-bonded carbon atoms bears at least one leaving group selected from the group consisting of iodide, bromide, chloride, azide, tosylate, mesylate, nosylate and triflate. Examples of suitable fluorinated alkenes include $^{18}F$—$CH$=$CI_2$, $^{18}F$—$CI$=$CH_2$, and $^{18}F$—$CI$=$CI_2$. These labeling reagents can be made by the F-18 fluorination of corresponding compounds, such as $ICH$=$CI_2$; $CI_2$=$CH_2$; $CI_2$=$CI_2$. Other fluorinated alkenes useful in accordance with the present invention will be apparent to those skilled in the art.

F-18 can be obtained from cyclotrons after bombardment of O-18-enriched water with protons. The enriched water containing H—$^{18}F$ can be neutralized with a base having a counter-ion that is any alkali metal (M), such as potassium or another monovalent ion, and the water can be evaporated off to give a residue of M—$^{18}F$, which can be taken up in an organic solvent for further use. In general, the counter-ion is selected to enable the fluoride ion to react rapidly in an organic phase with a halogen. Potassium is generally used as a counter-ion because it is cheaper than cesium. However, with carrier-free F-18, trivial amounts of counter-ion are required, and counter-ion cost largely can be ignored.

Although potassium is useful as a counter-ion in accordance with the present invention, cesium is preferred to potassium because cesium is a larger ion with a more diffuse charge. Accordingly, cesium has looser ionic interactions with the small fluoride atom, and therefore does not interfere with the nucleophilic properties of the fluoride ion. For similar reasons, potassium is preferred to sodium, and, in general, the suitability of a Ia metal as a counter-ion in accordance with the present invention increases as you go down the periodic table. Group Ib reagents, such as silver, also are useful as counter-ions in accordance with the present invention. Further, organic phase transfer-type ions, such as tetraalkylammonium salts, also can be used as counter-ions.

Because fluoride is the most electronegative element, it has a tendency to become hydrated and lose its nucleophilic character. To minimize this, the labeling reaction is preferably performed under anhydrous conditions. For example, fluoride (as potassium fluoride or as a complex with any of the other counter-ions discussed above) can be placed in organic solvents, such as acetonitrile or THF. With the help of agents which bind to the counter-ion, such as Kryptofix 2.2.2 (4,7,13,16,21,24-hexaoxa-1,10-diazabicyclo[8.8.8]-hexacosane), the fluoride ion is very nucleophilic in these solvents.

As discussed above, the labeling reagent is used to label targeting vectors comprising a thiol-containing peptide with F-18 according to the following reaction:

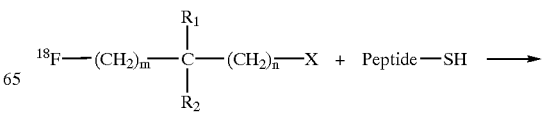

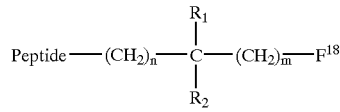

Alternatively, the labeling reagent is a F-18 fluorinated alkene, wherein at least one of the two double-bonded carbon atoms bears at least one leaving group selected from the group consisting of iodide, bromide, chloride, azide, tosylate, mesylate, nosylate and triflate. This F-18 fluorinated alkene labels targeting vectors in an analogous manner to the reaction set forth above.

Directing the reaction of the fluorinated labeling reagent towards free thiol groups on the targeting vector allows near-quantitative incorporation of F-18 into the targeting vector within a short time period. Generally, the reaction will be completed within a few minutes at room temperature, and complicated purification steps will not be necessary. Given the very short half-life of F-18, the speed of the reaction is very important. Moreover, because free F-18 exchanges readily with hydroxyl ions in hydroxyapatite crystals in bone, and, therefore, is a bone-seeking agent, the reduced amount of free fluoride remaining in the final product also is an important advantage of the present invention.

The embodiments of the invention are further illustrated through examples which show aspects of the invention in detail. These examples illustrate specific elements of the invention and are not to be construed as limiting the scope thereof.

EXAMPLES

Fluorodiiodoacetic acid ($^{18}$F—CI$_2$COOH)

100 mCi of F-18 fluoride (obtained from bombardment of O-18-enriched water) in dry tetrahydrofuran containing Kryptofix 2.2.2 (4,7,13,16,21,24-hexaoxa-1,10-diazabicyclo[8.8.8]hexacosane) and a slurry of potassium carbonate is treated with triiodoacetic acid. After a 30 minute reaction at room temperature, the desired labelling reagent, $^{18}$F—CI$_2$COOH, is obtained and purified by reverse-phase column chromatography. This labelling reagent is then used to label a variety of thiol-containing targeting vectors, or is shipped to clinical sites for the same usage.

F-18-Labeled Fab'-SH Fragment

A 1 mg vial of lyophilized Fab'-SH-NP4 (an anti-carcinoembryonic antigen antibody fragment) is reconstituted with 1 mL of a solution of $^{18}$F—CI$_2$COOH in 0.1 M sodium acetate buffer at pH 6. The reaction is allowed to proceed for 30 minutes at room temperature.

An aliquot of the mixture is removed for analysis by HPLC using a size-exclusion sizing column and by ITLC (instant thin-layer chromatography) using silica gel-impregnated glass-fiber strips (Gelman Sciences). This analysis reveals that the antibody fragment's hinge-region thiol groups effect nucleophilic displacement of both iodine atoms of $^{18}$F—CI$_2$COOH, and that this reaction proceeds in near-quantitative yield. The F-18-labeled Fab' fragment is therefore ready for injection.

Fluorodiiodomethane ($^{18}$F—CHI$_2$)

A sample of 100 mCi of F-18 fluoride (obtained from bombardment of 0–18-enriched water) in dry acetonitrile containing Kryptofix 222 and a slurry of potassium carbonate is treated with triiodomethane. After a 30 minute reaction at room temperature the labelling reagent $^{18}$F—CHI$_2$ is obtained and purified by reverse-phase column chromatography. The labelling reagent is then used to label a variety of thiol-containing targeting vectors, or is shipped to clinical sites for the same usage.

F-18-Labeled Octreotide

A 1 mg vial of lyophilized, reduced octreotide (D-Phe-Cys-Phe-D-Trp-Lys-Thr-Cys-Thr-ol) is reconstituted with 1 mL of a solution of $^{18}$F—CHI$_2$ (made up first in DMSO) in 0.1 M sodium acetate buffer at pH 6, containing 20% DMSO. The reaction is allowed to proceed for 30 minutes at room temperature. Alternatively, can be effected at elevated temperatures, and in non-aqueous solvents, e.g., DMSO, and later cooled and/or diluted for injection.

An aliquot of the labeling mixture is removed for analysis by HPLC using a size-exclusion sizing column and ITLC (instant thin-layer chromatography) using silica gel-impregnated glass-fiber strips (Gelman Sciences). This analysis reveals that the two cysteinyl thiol groups of octreotide effect the nucleophilic displacement of both iodo atoms of $^{18}$F—CHI$_2$, and that this reaction proceeds in near-quantitative yield. The F-18-labeled, recyclized (linkage: —S—CH—$^{18}$F—S—) octreotide peptide is therefore ready for injection.

Fluorodiiodoacetamide ($^{18}$F—CI$_2$CONH$_2$)

100 mCi of F-18 fluoride (obtained from bombardment of O-18-enriched water) in dry tetrahydrofuran containing Kryptofix 2.2.2 (4,7,13,16,21,24-hexaoxa- 1,10-diazabicyclo[8.8.8]hexacosane) and a slurry of potassium carbonate is treated with triiodoacetamide. After a 30 minute reaction at room temperature, the desired labelling reagent, $^{18}$F—CI$_2$CONH$_2$, is obtained and purified by reverse-phase column chromatography. This labelling reagent is then used to label a variety of thiol-containing targeting vectors, or is shipped to clinical sites for the same usage.

F-18-Labeled Cys-LHRH

A 1 mg vial of lyophilized Cys-LHRH (LHRH whose amine terminus bears an appended cysteine, in reduced, thiol, form) reconstituted with 1 mL of a solution of $^{18}$F—CHICONH$_2$ in 0.1 M sodium acetate buffer at pH 6. The reaction is allowed to proceed for 2 hours at 50° C. The antibody modified peptide's thiol group effects nucleophilic displacement of the iodo atom of $^{18}$F—CIHCONH$_2$, and the reaction proceeds in near-quantitative yield. The F-18-labeled peptide is ready for injection.

It will be apparent to those skilled in the art that various modifications and variations can be made to this invention. Thus, it is intended that the present invention cover the modifications and variations of this invention provided they come within the scope of the claims and their equivalents.

What is claimed is:

1. A method for detecting a tissue comprising:
   (a) administering to a patient a bispecific antibody or antibody fragment comprising an arm that is specific to a target tissue of the patient and another arm that is specific to an F-18-labeled peptide or a low molecular weight hapten conjugated to the F-18-labeled peptide; and allowing the bispecific antibody or antibody fragment to bind to the target tissue, and the non-targeted bispecific antibody or antibody fragment to clear;
   (b) administering the F-18-labeled peptide or the hapten conjugate thereof to the patient, and allowing the F-18-labeled peptide or the hapten conjugate thereof to bind to the bispecific antibody or the antibody fragment, and the unbound F-18-labeled peptide or hapten conjugate thereof to clear; and
   (c) detecting the F-18-labeled peptide, thereby detecting the target tissue.

2. The method according to claim 1, wherein the F-18-labeled peptide contains a thiol group.

3. The method according to claim 2, wherein the F-18-labeled peptide is labeled by a method comprising reacting a peptide comprising a free thiol group with a labelling regent having the general formula $^{18}F-(CH_2)_m-CR_1R_2-(CH_2)_n-X$, wherein:

n is 0, 1 or 2;

m is 0, 1 or 2;

and n+m is 0, 1, or 2;

X is selected from the group consisting of iodide, bromide, chloride, azide, tosylate, mesylate, nosylate, triflate, unsubstituted maleimide, maleimide substituted with one or two alkyl groups, and 3-sulfo-maleimide; and $R_1$ and $R_2$ are the same or different and are selected from the group consisting of iodide, bromide, chloride, azide, tosylate, mesylate, nosylate, triflate, hydrogen, $-CONH_2$, carboxyl, hydroxyl, sulfonic acid, tertiary amine, quaternary ammonium, unsubstituted alkyl, substituted alkyl, $-COOR'$, $-CONR'_2$, or $COR'$, wherein the substituents of the substituted alkyl groups are selected from the group consisting of $-CONH_2$, carboxyl, hydroxyl, sulfonic acid, tertiary amine and quaternary ammonium and wherein R' is a $C_1-C_6$ alkyl or phenyl.

4. The method according to claim 2, wherein the F-18-labeled peptide is labeled by a method comprising reacting a peptide comprising a free thiol group with a F-18 fluorinated alkene, wherein at least one of the two double-bonded carbon atoms bears at least one leaving group selected from the group consisting of iodide, bromide, chloride, azide, toyslate, mesylate, nosylate and triflate.

5. The method according to claim 1, wherein the F-18-labeled peptide is X-Gly-D-Tyr-D-Trp-Gly-D-Lys(X)-Gly-D-Tyr-D-Trp-OH, and X represents a free or protected amino acid group.

6. The method according to claim 1, wherein the F-18-labeled peptide is Ac-Cys(Y)-D-Tyr-D-Trp-Gly-D-Cys(Y)-Gly-D-Tyr-D-Trp-OH, and Y represents a free or protected thiol group.

7. The method according to claim 1, wherein the F-18-labeled peptide is Ac-Gly-D-iodo-Tyr-D-Trp-Gly-D-Lys(Ac)-Gly-D-iodo-Tyr-D-Trp-OH.

8. The method according to claim 1, wherein the hapten is a metal chelate complex.

9. The method according to claim 8, wherein the metal chelate complex comprises manganese, iron, or gadolinium.

10. The method according to claim 1, wherein the bispecific antibody or antibody fragment is monoclonal.

11. The method according to claim 1, wherein the antibody or antibody fragment is humanized.

12. The method according to claim 1, wherein the F-18-labeled peptide is detected by position emission tomography.

* * * * *